(12) United States Patent
Deka et al.

(10) Patent No.: US 6,368,864 B1
(45) Date of Patent: Apr. 9, 2002

(54) DYES AND METHODS OF RETICULOCYTE ENUMERATION

(75) Inventors: Chiranjit Deka, Miami; Song Y. Lee, Davie, both of FL (US); Gene G.-Y. Shen, Diamond Bar, CA (US); Stephen Szydlo, Miami, FL (US); Tsong-Tseh Tsay, Orange, CA (US); Ravinder Gupta, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/566,298

(22) Filed: May 5, 2000

(51) Int. Cl.[7] ............................. G01N 31/00; G01N 33/48
(52) U.S. Cl. ........................ 436/10; 436/8; 436/63; 436/166; 436/172; 436/800; 252/408.1; 435/2; 435/29; 435/34
(58) Field of Search ......................... 436/8, 10, 63, 436/164, 166, 172, 174, 800; 252/408.1; 435/2, 29, 30, 34

(56) References Cited

U.S. PATENT DOCUMENTS

| | | | |
|---|---|---|---|
| 4,386,146 A | * 5/1983 | Kishino et al. | 430/95 |
| 4,883,867 A | 11/1989 | Lee et al. | 536/28 |
| 4,957,870 A | 9/1990 | Lee et al. | 436/63 |
| 5,312,921 A | * 5/1994 | Glazer et al. | 546/108 |
| 5,321,130 A | * 6/1994 | Yue et al. | 536/23.1 |
| 5,360,739 A | 11/1994 | Fan et al. | 436/63 |
| 5,411,891 A | 5/1995 | Fan et al. | 436/63 |
| 5,436,134 A | * 7/1995 | Haugland et al. | 435/34 |
| 5,563,070 A | 10/1996 | Yamamoto et al. | 436/63 |
| 5,599,932 A | * 2/1997 | Bieniarz et al. | 544/361 |
| 5,633,167 A | 5/1997 | Fan et al. | 436/17 |
| 5,639,666 A | 6/1997 | Shenkin | 436/63 |
| 5,658,751 A | * 8/1997 | Yue et al. | 435/34 |
| 5,773,299 A | 6/1998 | Kim et al. | 436/63 |
| 5,821,127 A | 10/1998 | Akai et al. | 436/10 |
| 5,863,753 A | * 1/1999 | Haugland et al. | 435/34 |
| 5,994,138 A | 11/1999 | Veriac | 436/10 |

FOREIGN PATENT DOCUMENTS

| | | | |
|---|---|---|---|
| EP | 634640 | * | 1/1995 |
| EP | 1 004 880 A2 | | 5/2000 |

OTHER PUBLICATIONS

H. Shapiro, Practical Flow Cytometry, 3rd edit., 1995; Wiley–Liss, New York.
Davis, et al., (1990) *Pathobiol.*, 58:99–106.
Hoy, (1990) *Bailliere's Clin. Haemat.*, 3:977–997.
H.J. Tanke, *Flow Cytometry in Hematology* (1992), Academic Press Ltd., pp. 75–93.
Seligman, et al., *Am. J. Hematology*, 14:57–66 (1983).
Lee, et al. *Cytometry*, 7:508–517 (1986).

* cited by examiner

*Primary Examiner*—Maureen M. Wallenhorst
(74) *Attorney, Agent, or Firm*—Mary E. Bak; Mitchell E. Alter

(57) ABSTRACT

A dye compound having the formula I:

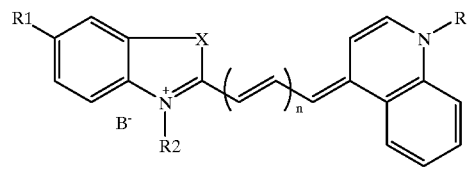

wherein,
n is 0, 1, 2, or 3; R1 is H, alkyl, or an alkoxy group; R2 is $CH_2(CH_2)_mOH$, wherein m is 0, 1, 2, or 3; X is O, S, or $C(CH_3)_2$; R is $CH_3$, $CH(CH_3)_2$, $CH_2CH_2OH$, alkyl, alkylsulfonate, or hydroxyalkyl and B– is a counteranion.

Red- and blue-excitable dyes based on the above chemical structure are described, and reagents containing them are described for use in staining nucleic acid, more particularly for staining reticulocytes. Also described are methods for detecting reticulocytes using such compositions.

34 Claims, 7 Drawing Sheets

1

DYES AND METHODS OF RETICULOCYTE ENUMERATION

FIELD OF THE INVENTION

This invention generally relates to the field of new dyes, dye compositions, and methods of enumeration of reticulocytes by flow cytometry by employing fluorescent, RNA binding dyes.

BACKGROUND OF THE INVENTION

Enumeration of reticulocytes, i.e., the immature erythrocytes, in human peripheral blood is a valuable component of diagnostic hematology. Such enumeration is useful in the diagnoses of hemorrhage, anemia, monitoring bone marrow transplantation and for monitoring patients undergoing chemotherapy and other disorders involving blood cell production [U.S. Pat. No. 5,360,739; H. Shapiro, Practical Flow Cytometry, $3^{rd}$ edit., 1995; Wiley-Liss, New York; Davis et al, (1990) *Pathobiol.*, 58:99–106; Hoy, (1990) *Bailliere's Clin. Haemat.*, 3:977–988; H. J. Tanke, Reticulocytes and Mature Erythrocytes in *Flow Cytometry in Haematology* (1992) Academic Press Ltd, pp. 75–93]. Because reticulocytes contain ribonucleic acid (RNA), if stained with RNA binding excitable dyes, these cells fluoresce when illuminated by a light source of appropriate wavelength. RNA binding dyes have been used to distinguish reticulocytes from mature red blood cells (RBCs) which lack RNA.

Distribution of fluorescence intensities of a relatively large reticulocyte population can be determined by flow cytometry in a fast and reliable manner, and different maturation stages of reticulocytes, as reflected by differences in RNA content, can be distinguished.

The use of red-excitable dyes is desirable because such dyes are detected by excitation with relatively inexpensive diode or HeNe lasers. However, initial efforts in the prior art to employ diode lasers and red-excited dyes for rapid flow cytometric analyses of reticulocytes were not successful. Yamamoto, U.S. Pat. No. 5,563,070 suggested that the addition of large quantities of TO-PRO-3, a red-excitable dye, followed by a 30 minute incubation, stained RNA inside living reticulocytes. Such a method, however, is not practical for routine analysis of reticulocytes in clinical laboratories that require high sample throughput because sample preparation time is long and cost per test is high due to the large amount of dye required to stain each sample.

A red-excitable dye called Thiazole Blue (TB) has been described in U.S. Pat. No. 4,957,870. However, as described in this patent (U.S. Pat. No. 4,957,870), this dye also requires long periods of incubation, of about 30 minutes.

Akai et al., U.S. Pat. No. 5,821,127 have also described the preparation of fluorescent dyes which are capable of detecting reticulocytes using inexpensive detectors via fluorescence in the red region. However the samples require incubation at elevated temperatures of about 40° C.

More recently, U.S. Pat. No. 5,994,138, described staining reticulocytes via the use of a red-excitable dye in combination with a detergent and an ionophore at elevated temperatures of about 35° C. However, staining reticulocytes was not successful when ambient temperatures were utilized.

Fan et. al (U.S. Pat. Nos. 5,411,891, 5,360,739) describes clearly that the specific binding constant between a dye and reticulocyte RNA and the rate of penetration of the dye are different for each dye and that it is impossible to predict under what conditions a particular dye may rapidly penetrate red cell membrane and stain reticulocytes. This was further supported by Akai et. al (U.S. Pat. No. 5,821,127).

Thus, there exists a need in the art for dyes, compositions and methods which enable rapid staining of intracellular RNA at room temperatures via the use of dyes that are excitable in the red region and can use inexpensive and readily available red-illumination instruments. In addition there exists a need in the art for dye compositions and methods that are applicable not only to red-excitable dyes, but also to dyes excitable at other wavelengths, such as in the blue wavelength. By doing so, ready and accurate detection of reticulocytes can be accomplished without particular restriction of the excitation wavelength.

SUMMARY OF THE INVENTION

In one aspect, the present invention provides novel dyes of the formula:

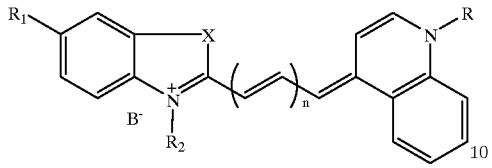

wherein n is 0, 1, 2, or 3; $R_1$ is H, alkyl, or an alkoxy group; $R_2$ is $CH_2(CH_2)_mOH$, wherein m is 0 to 3; X is O, S, or $C(CH_3)_2$; R is $CH_3$, $CH(CH_3)_2$, $CH_2CH_2OH$, alkyl, alkysulfonate, or hydroxyalkyl; and $B^-$ is a counteranion.

In another aspect, the invention provides a reagent containing a dye of the invention and a solvent.

In yet another aspect, the invention provides compositions and methods for facilitating rapid transport of dye molecules through a cell membrane. This composition contains the dye of this invention and at least one member selected from the group comprising a detergent, a surfactant, a sulfonic acid or a salt thereof.

Other aspects and advantages of this invention will be readily apparent from the detailed description of the invention.

BRIEF DESCRIPTION OF THE DRAWINGS

FIG. 2A shows fluorescence from cells treated with ReticRed1 alone and incubated for about 10 min: Total count 42660, Red cells 32841, Reticulocytes 801, calculated retic percentage 2.4%. FIG. 2B shows fluorescence from cells treated with ReticRed1 alone and incubated for about 40 min: Total count 46199, Red cells 39713, Reticulocytes 2310, calculated retic percentage 5.8%. The reference value for reticulocyte in this sample was approximately 7%.

DETAILED DESCRIPTION OF THE INVENTION

Figure 1A:
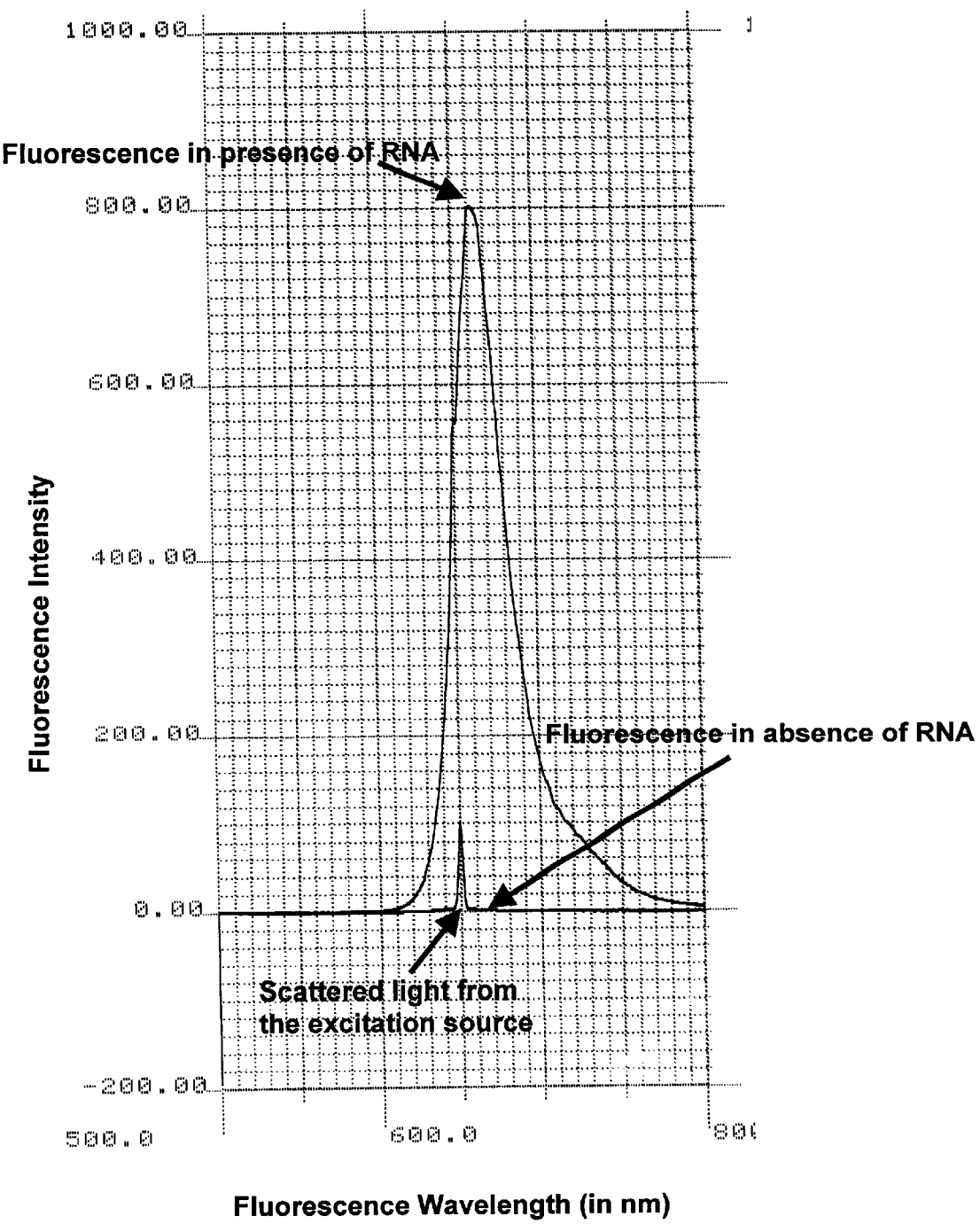
FIG. 1A is the comparison of the fluorescence spectra of the dye compound No. 6 described in example 1, hereinafter called ReticRed1, in PBS solution with or without RNA present in the solution.

The present invention provides dyes for staining nucleic acids, as well as compositions and methods to facilitate rapid transport of dyes through cell membranes for staining reticulocytes. Advantageously, the dyes of the invention are characterized by exhibiting significantly stronger fluorescence when bound to nucleic acids than when unbound.

In a preferred embodiment, suitable samples containing reticulocyte cell populations for analyses using the dyes, compositions and methods of the present invention are preferably selected from whole blood, or blood samples that have been enriched or depleted by certain additional processes prior to staining. Such enrichment or depletion processes may include, among others, centrifugation, ficoll assisted gravity separation or magnetic separation.

Advantageously, the dyes, methods and compositions of the invention do not require cell fixation and are therefore particularly well suited for use in analyses of metabolically active cells. However, selection of the cell population is not a limitation on the present invention.

As discussed above, only a few dyes, which have the ability to fluoresce in the red or blue region, are suitable for reticulocyte enumeration. These dyes, however, require the use of elevated temperatures, necessitate long incubation periods, create large amounts of non-specific background fluorescence, and/or show little enhancement of fluorescence in presence of RNA. The present invention provides novel dyes, both red and blue-excitable, which bind nucleic acids and permit detection of reticulocytes via fluorescence at ambient temperatures. Suitably, the dyes of the invention are adapted to methods which preferentially permit rapid detection of reticulocytes in the absence of substantial background fluorescence. An advantage of the method of the invention is the speed at which the staining is accomplished and the fact that it can be achieved using whole blood at room temperature.

The dyes of the invention has the formula (hereinafter called general formula):

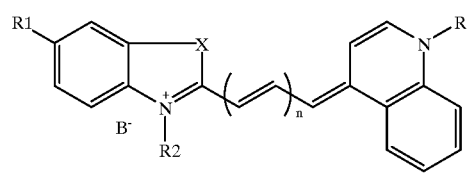

wherein n is 0, 1, 2 or 3; $R_1$ is H, alkyl, or an alkoxy group; $R_2$ is $CH_2(CH_2)_m OH$, wherein m is 0, 1, 2, or 3; X is O, S, or $C(CH_3)_2$; R is $CH_3$, $CH(CH_3)_2$, $CH_2CH_2OH$, alkyl, alkylsulfonate, or hydroxyalkyl; and $B^-$ is a counteranion.

According to the invention, a counterion includes, without limitation, a single element or a negatively charged group. In one embodiment of the invention, the counteranion is a halide selected from among $Br^-$, $Cl^-$ or $I^-$. In another embodiment of the invention, the counteranion is a tosylate group ($OTs^-$), wherein $OTs^-$ is $[CH_3(C_6H_4)SO_3]^-$. However, the invention is not so limited. It is within the skill of one in the art to select a suitable counteranion, from among those known ions and ionic groups, including, without limitation, $PF_6^-$, and $BF_4^-$.

The invention provides dye compounds having the general formula given above, which may be either red-excitable or blue-excitable dyes. As used herein, a red excitable dye is a dye which fluoresces when illuminated with light of a wavelength in the red spectral range. As used herein, this red spectral range is from about 600 nm to about 725 nm, and preferably, 630 nm to 670 nm. A blue excitable dye is a dye which fluoresces when contacted with light of a wavelength in the blue spectral range. As used herein, a blue excitable dye can typically have an absorption maximum in the range of 420 nm to 560 nm, and preferably from about 450 nm to about 520 nm.

As stated above, the dyes of the invention are characterized by exhibiting stronger fluorescence when bound to nucleic acids than when unbound. Generally, the dyes of the invention have a fluorescence enhancement ratio of greater than about 200 (ratio of fluorescence intensity of RNA-bound dye to fluorescence intensity of free dye). In some embodiments, the dyes of the invention have a fluorescence enhancement ratio of greater than about 300. Still other dyes of the invention will have a fluorescence enhancement ratio of greater than about 350, yet other dyes of the invention will have a fluorescence enhancement ratio of greater than about 400, and still other dyes of the invention will have a have a fluorescence enhancement ratio of greater than about 450. For specific examples, see, e.g., FIG. 1B and Table 1. However, the present invention is not limited by the ratios provided herein.

In one desirable embodiment, the invention provides a dye, termed herein, ReticRed1 having the following formula.

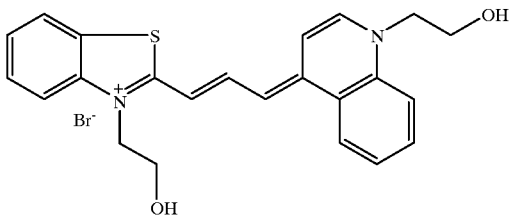

ReticRed1 is further described in Example 1A, compound (6). With reference to the general formula, in ReticRed1, n is 1, R1 is H, R2=CH$_2$CH$_2$OH, R=CH$_2$CH$_2$OH, X is S, and B$^-$ is Br$^-$.

In another desirable embodiment, the invention provides a dye, termed ReticRed2, having the formula:

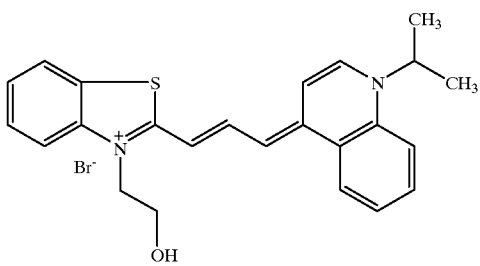

With reference to the general formula, in ReticRed2 n is 1, R$_1$ is H, R is CH(CH$_3$)$_2$, X is S, R$_2$ is CH$_2$CH$_2$OH, and B$^-$ is Br$^-$.

In yet another desirable embodiment, the invention provides a dye, termed ReticRed3, having the formula:

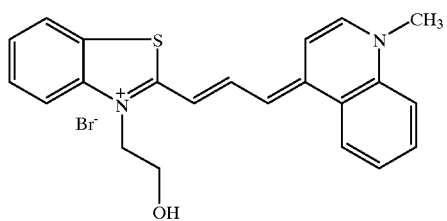

With reference to the general formula, in ReticRed3 n is 1, R$_1$ is H, R is CH$_3$, R$_2$ is CH$_2$CH$_2$OH, X is S, and B$^-$ is Br$^-$.

In still another desirable embodiment, the invention provides a dye, termed ReticRed4, having the formula:

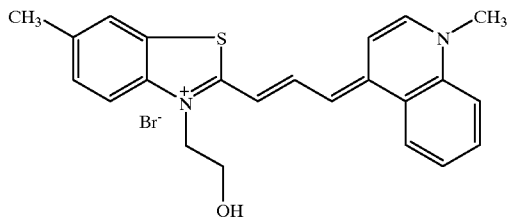

With reference to the general formula, in ReticRed4, n is 1, R$_1$ is CH$_3$, R is CH$_3$, R$_2$ is CH$_2$CH$_2$OH, X is S, and B$^-$ is Br$^-$.

In a further embodiment, the invention provides a dye, termed ReticRed5, having the formula:

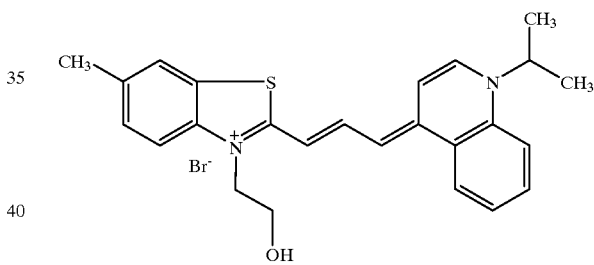

With reference to the general formula, in ReticRed5, n is 1, R$_1$ is CH$_3$, R is CH(CH$_3$)$_2$, R$_2$ is CH$_2$CH$_2$OH, X is S, and B$^-$ is Br$^-$.

In another desirable embodiment, the invention provides a dye, termed ReticRed6, having the formula:

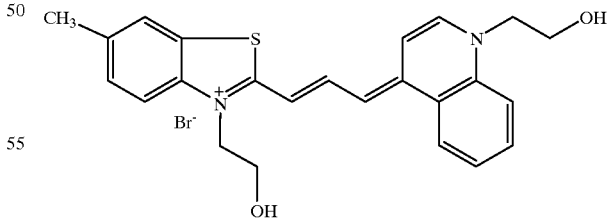

With reference to the general formula, in ReticRed6, n is 1, R$_1$ is CH$_3$, R is CH$_2$CH$_2$OH, R$_2$ is CH$_2$CH$_2$OH, X is S, and B$^-$ is Br$^-$.

In yet another desirable embodiment, the invention provides a blue-excitable dye, termed ReticBlue1, where with reference to the general formula, n is 0. One particularly desirable example of a preferred blue excitable dye is ReticBlue1, which is represented by the general formula, wherein, n=0, R1=H, m=1, R2=CH$_2$CH$_2$OH, R=CH$_2$CH$_2$OH, X=S, B$^-$=Br$^-$.

The dyes of the invention are useful for a variety of purposes which will be readily apparent to those of skill in the art. Such uses include, for example, use of dyes as markers or tags for detecting the presence of a molecule or compound to which they are bound. Such markers may be used for monitoring the efficacy of a therapeutic compound in vivo or for diagnostic uses, or the like. However, the dyes of the invention are particularly well suited for staining of nucleic acids. For example, these dyes are particularly suitable for staining of RNA in reticulocytes. Typically, when used in staining of nucleic acids, the dyes are formulated into reagent solutions.

I. Staining Reagents

The invention provides a variety of compositions, described herein, which are useful as staining reagents in a variety of applications, including a variety of assay formats. Examples of such uses will be readily apparent to those of skill in the art, upon a review of the compositions described herein.

A. Dye Compositions

In order to utilize the novel dyes of the invention for staining of nucleic acids, the dyes are dissolved in an appropriate solvent to form solutions. As defined herein, a solvent is meant to describe any liquid that can dissolve a solid, liquid, or gas. A preferred embodiment of the invention utilizes water-based or miscible liquids, such as dimethylsulfoxide (DMSO), methanol, ethanol, and mixtures thereof. Selection of a suitable solvent is however not a limitation on the present invention. For storage, typically a relatively high concentration of the dye is dissolved in a suitable solvent to obtain a stock solution. In a preferred embodiment, to obtain a stock solution of the dye, the dye is dissolved in DMSO at a dye concentration ranging from 0.5 mM to 10 mM, and most preferably, 1 to 5 mM.

For further application of the dye composition in the method of the invention, the stock solution may be diluted in other reagents or buffers, including, for example, water, saline, phosphate buffered saline (PBS), or isotonic saline. The final dye concentration in such dye compositions may be varied depending on the application. In one embodiment, the concentration of the dye in the final dye composition added to a sample of whole blood is in the range of about 0.1–50 μM, preferably from about 0.5 to 25 μM, and more preferably 2 to 10 μM. However, selection of an appropriate concentration or diluting solvent is not a limitation on the present invention.

The dye composition of the invention can be utilized for a variety of purposes. A preferred embodiment of this invention is the use of the dye composition for staining, detection, and analysis of nucleic acids. Another preferred embodiment of this invention is the use of the dye composition for staining, detection, and analysis of reticulocytes in whole blood. One of skill in the art will readily understand that use of the dyes and reagents of the present invention is not so limited. In one particularly desirable embodiment, for example, where the dye contacts intact cells, it can be desirable to formulate one or more of the dyes into a mixture.

B. Compositions for Rapid Staining

In another aspect, a dye composition of the invention may be utilized to facilitate rapid transport of the dyes through the cell membrane, thereby permitting the dye to stain reticulocytes in about 1 minute or less. Thus, the method of the invention can permit staining in about 0 to about 60 seconds, preferably from about 0 seconds to about 45 seconds, more preferably from about 0 seconds to about 30 seconds, most preferably from about 0 seconds to about 20 seconds.

Generally, such rapid staining requires that a sample be contacted with a dye composition of the invention in the presence of at least one surfactant and optionally, a sulfonic acid or a salt thereof.

When used for rapid staining, additional components may be added to the composition of the invention. For example, buffers may be employed in situations where maintaining the pH of the dye composition is necessary. Preferably, the pH of the dye reagent is maintained in the range of about 6 to about 9. More preferably, a pH in the range of about 7 to about 7.5 is obtained. The buffer may be selected from a variety of buffers known to those of skill in the art to be used in the compositions of the invention and include, without limitation, phosphate buffered saline (PBS) or isotonic saline, such as ISOTON®II, U.S. Pat. No. 3,962,125, Coulter Corporation, Miami, Fla., or the like. Additionally, such buffers may also be used to adjust the concentration of one or more of the components of the composition of this invention. Preservatives may also be added to the compositions of the invention, and may be selected from, but is not limited to, 5-Chloro-2-methyl-4-isothiazolin-3-one, and 2-methyl-4-isothiazolin-3-one [such preservatives may be purchased commercially, e.g., as ProClin 300 or ProClin 150].

At least one surfactant is used in the rapid staining composition. In one exemplary embodiment, the surfactants include a detergent and a second surfactant which functions as a sphering agent for a cell. In another exemplary embodiment, the surfactants may be designed such that a single surfactant functions as both a detergent and a sphering agent. In yet another exemplary embodiment, the surfactants may be designed such that a single surfactant provides the necessary surfactant function, but no sphering reagent function is required.

Surfactants to be used in the composition of the invention may be selected from among the anionic surfactant ammonium perfluoralkyl carboxylate [commercially available as Fluorad FC-143 (3M Company, Minneapolis, Minn.)], sodium lauroyl myristoyl lactylate [commercially available as Pationic 138C (R.I.T.A Corp, Woodstock, Ill.)], or from the non-ionic surfactants Dodecyl-β-D-maltoside, N,N-bis [3-D-glucon-amidopropyl] cholamide, polyoxypropylene-polyoxyethylene block copolymer, N-Tetradecyl-β-D-maltoside, Daconyl-N-methyl-glucamide, n-Dodecyl-β-D-glucopyranoside, n-Decyl-β-D-glucopyranoside, polyethylene glycol ester of stearic acid, ethoxylated cocomonoglyceride, octyphenoxypoly (ethyleneoxy) ethanol, ethoxylated octylphenol, and linear alcohol, or, from among the cationic surfactants, coco hydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-dodecyl-N,N-dimethyl-3-ammonio-1-propanesulfonate, N-tetradecyl-N,N-dimethyl-3-ammonio-1-propanesulfonate.

As discussed above, the surfactant selected may function as a sphering agent for red cells when the concentration an osmolarity is appropriately adjusted. A sphering agent may be readily selected by one of skill in the art. A preferred sphering reagent is based on the non-ionic surfactant Dodecyl-β-D-maltoside, which suitably is in solution with a buffer such as phosphate buffered saline. To effectively isovolumetrically sphere the reticulocytes and red blood cells within a blood sample, the concentration of the sphering reagent in the composition is most preferably from about 3 μg/ml to about 50 μg/ml with a mOSm in the range of about 200 to about 400 mOSm, and preferably from about 250 mOSm to about 350 mOSm. However, one of skill in the art may readily adjust this concentration and osmolarity as needed or desired to isovolumetrically sphere the cells, taking into consideration the surfactant selected. As discussed above, optionally, the selection of the sphering reagent may eliminate the need for the detergent.

In one embodiment, a detergent is included in the dye composition of the invention. Detergents to be used are selected from among non-ionic detergents. Desirably, these detergents are used at a concentration between about 0 to about 1%. In one preferred embodiment of the invention, the detergents are used at concentrations of between about 0.001% to about 0.5%, and in a more preferred embodiment are in the range from about 0.01% to 0.1%. One currently preferred detergent is octypenoxypoly(ethyleneoxy)ethanol [commercially available as Igepal CA630 (Sigma N-6507) or Nonidet P-40 (Sigma)]. Examples of other suitable detergents include, ethyoxylated octylphenol [commercially available as Triton X-100 (Sigma T9284)], and linear alcohol alkoxylates [commercially available as Plurafac A-38 (BASF Corp) or Plurafac A-39 (BASF Corp)]. Typically, these detergents are mixed with a sample (or vice versa), e.g., 1–2 μl of whole blood or the like, or separately formulated into a composition of the invention.

In one desirable embodiment, a sulfonic acid, or a salt thereof, is included in the composition of the invention. The sulfonic acid or salt thereof acts as a further facilitator of transporting the dye composition through the membrane of the reticulocytes, and is used at a concentration ranging from about 0 to about 250 μM, most preferably from 0 to about 50 μM. One embodiment of this invention utilizes p-toluenesulfonic acid. In other embodiments of this invention, a p-toluenesulfonate salt can be substituted for p-toluenesulfonic acid. Examples of such salts include sodium, potassium, silver, zinc, and barium p-toluenesulfonate salts. Some examples of such salts are commercially available, e.g., from Sigma-Aldrich. Other suitable sulfonates may be readily selected for use in the invention.

The dye compositions of the invention can contain a single dye, optionally in the presence of other dye. In one embodiment of the invention, a composition of the invention can contain one or more of ReticRed1, ReticRed2, ReticRed3, ReticRed4, ReticRed5, ReticRed6, or ReticBlue1 or any combination thereof.

In yet another embodiment of the invention, the composition of the invention can contain other dyes known to those of skill in the art in combination with one or more of the novel dyes of the invention. Such dyes are readily selected from among dyes which have been published and/or which are commercially available. See, for example, Beckman Coulter, Inc. (Fullerton, Calif.) catalog. There are a variety of uses for the dyes and compositions of the invention, which will be readily apparent to one of skill in the art.

II. Methods of Staining Nucleic Acids using the Dyes of the Invention

The dye composition of the invention is useful in staining a variety of nucleic acids, including DNA and RNA.

In samples containing free nucleic acids, for example, nucleic acids not surrounded by an intact cell membrane of a cellular or non-cellular source, the dye composition of the invention can stain the nucleic acids. In one embodiment of the invention, a method is provided for contacting a sample containing nucleic acids with the dye compositions of the invention. Preferably, the method involves contacting a sample containing nucleic acids with a dye composition of the invention, optionally in the presence of other dyes and reagents known to those of skill in the art. In a preferred embodiment of the invention, the method involves contacting a sample containing nucleic acids with a dye composition of the invention, which contains about 2 to about 10 μM red excitable ReticRed1 dye and an isotonic aqueous buffer.

However, the dye compositions of the invention are particularly well suited for use in the detection and enumeration of reticulocytes, which contain RNA. The method of the invention therefore involves contacting a reticulocyte containing nucleic acid with one or more dye compositions of the invention.

In one embodiment, the method involves contacting the blood cells with a dye composition of the invention in the presence of at least one surfactant, optionally together with a preservative and sulfonic reagent. As described above, the surfactant(s) can include a detergent and/or a sphering agent. According to the method of the invention, the cells can be contacted with a composition containing these components. Alternatively, one or more of these components can be delivered separately, for example by adding the component (s) directly to the sample. The mixture is then incubated for a suitable period of time. As previously discussed, the incubation time will be less than 1 minute. However, if desired for purposes of convenience, the incubation period may be either extended or shortened. For example, by adjusting the concentration of the dye, surfactant or detergent, the incubation time can be increased to greater than 1 minute. Desirably, this mixing and incubation may be performed at room temperature (approximately 22° C. to 28° C.). However, in a preferred embodiment of this invention, temperatures ranging from 20° C. to 40° C., may be utilized.

In a currently preferred embodiment, the method of the invention requires incubation of the dye for a period ranging from above 0 seconds to about 1 minute to stain reticulocytes, and the staining can be accomplished at room temperatures. In another preferred embodiment, incubation time is eliminated because the blood sample is mixed with the dye composition and thereafter immediately analyzed by the instrument. See Example 5, FIG. 7 and FIG. 8. Prior art staining techniques using red-excitable dyes for reticulocytes in this time frame requires incubation at elevated temperatures and/or additional use of toxic ionophoric compounds.

Reticulocytes stained with the dye compositions, according to the method of the invention, are preferably enumerated in an automatic flow cytometer. However, these cells may also be counted by a manual procedure or automated microscopy.

Thus, the method of the invention facilitates transport of nucleic acid-specific dyes which are not readily cell membrane permeant in the time frame which is desirable for automated flow cytometry. Automatic flow cytometers are well known in the art, and the present invention is not limited to the use of any particular flow cytometer. A preferred embodiment of the invention entails the detection and enumeration of reticulocytes using the COULTER® XL™ flow cytometer [Beckman Coulter, Inc., Miami, Fla.].

Different analytical techniques can be employed in the enumeration of reticulocytes by flow cytometric measurements including, but not limited to light scatter, fluorescence, optical absorption, axial light loss, DC electrical impedance, and radio frequency (RF) conductivity. In a preferred embodiment of the invention, in using such flow cytometers, light scatter gates are used to isolate red cells, and fluorescent gates are then used to delineate reticulocytes from mature red cells and enumerate the reticulocytes. In another embodiment of the invention, using flow cytometers, DC and light scatter light scatter gates are used to isolate red cells, and fluorescent gates are then used to delineate reticulocytes from mature red cells and enumerate the reticulocytes. In yet another embodiment of the invention, using flow cytometers, DC and fluorescent measurement alone are used to delineate reticulocytes from mature red cells and enumerate the reticulocytes.

Another notable advantage of the preferred embodiment of the invention is that when the composition includes a red-excitable dye of the invention, such as ReticRed1 or ReticRed3, it permits the use of a less expensive excitation source than argon lasers used for other presently available reticulocyte dyes, such as CPO, AO [Seligman, *Am. J. Hematology*, 14:57 91983)], TO [Lee et. al., Cytometry, 7:508 (1986)], Auraniine-O and Pyronin-Y. For example, when the red-excitable dye composition of the invention is used, the present invention advantageously permits the use of a red laser as the excitation source. Specifically, a red diode laser, a high power light emitting diode (LED), or a red helium-neon laser can be used to conduct reticulocyte counting using a red-excitable dye reagent of this invention.

A variety of lasers are known to those of skill in the art that may be utilized as the excitation sources for the flow cytometers. The lasers may be selected from, but are not limited to, argon, helium-neon, diode, and diode pumped solid-state lasers, depending upon the excitation wavelength of the dye of the invention selected for detection of reticulocytes. Selection of suitable light sources, and appropriate excitation wavelengths, are not a limitation on the present invention.

Suitable excitation wavelengths may be readily determined by one of skill in the art. Examples of suitable excitation wavelengths in the red spectral range include those in the range of 600 nm to 725 nm, and preferably 630 nm to 670 nm. Other suitable excitation sources and wavelengths may be readily selected by one of skill in the art, taking into consideration the dye selected for use in the method and compositions of the invention. For example, the use of ReticBlue1, an analog of ReticRed1, can be excited in the blue region of the optical spectrum.

An additional advantage comes from the fact that red-excitable dye compounds of this invention such as ReticRed1, ReticRed2, ReticRed3, ReticRed4, ReticRed5, ReticRed6 etc. are essentially non-fluorescent in the unbound state. As a result, problems associated with background fluorescence are minimal, and reticulocytes can be detected with high specificity using this dye.

Thus, the present invention permits reticulocytes to be rapidly stained with the dyes of the invention for subsequent flow analysis. The method of the invention differs from both the prior art Pyronin-Y [Tanke et al, cited above] staining procedure requiring fixation of the cells and the prior art fluorescence staining procedures involving membrane permeable dyes such as CPO (ReticOne™) or Thiazole Orange (ReticCount™) that does not require cell-fixation, but requires long incubation with the blood to accomplish staining.

III. EXAMPLES

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

Example 1

Materials and Methods

A. General Dye Synthesis

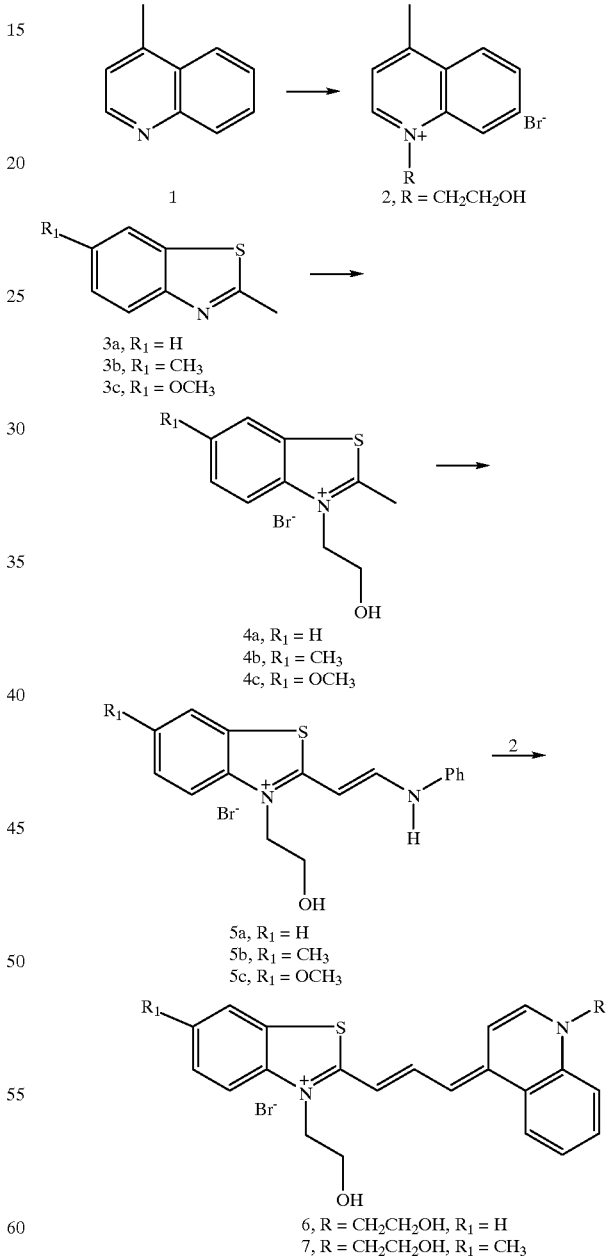

B. Specific Dye Preparation

Preparation of 1-(2-Hydroxy)ethyllepidinium Bromide (2). A solution of lepidine (11.5 g) and bromoethanol (100 g) were stirred and heated in an oil bath at 110° C. for 48 hours. Cooling the reaction mixture to room temperature, adding ethyl acetate (100 ml) and stirring for 5 min resulted in a solid that was collected, washed with ethyl acetate (2×20 ml) and dried. The solid was then dissolved in methanol (80 ml) and precipitated with ethyl acetate (600 ml). The solid was collected via filtration, washed with ethyl acetate (2×100 ml) and dried in an oven under high vacuum at 50° C. overnight to obtain 11.47 g (53% yield) of product (2c).

Preparation of 3-(2-Hydroxy)ethyl-2-methylbenzothiazolium Bromide (4a). A solution of 2-methylbenzothiazole (5.87 g) and 2-bromoethanol (49.2 g) was stirred and heated in an oil bath at 110° C. for 18 hours. After cooling the reaction mixture to room temperature, adding ethyl acetate (100 ml), and decanting, the resultant solid was then dissolved in methanol (50 ml) and precipitated with ethyl acetate (300 ml). The solid was again recrystallized from a mixture of methanol and ethyl acetate, washed with ethyl acetate (2×25 ml) and dried in an oven under high vacuum at 50° C. overnight to obtain 4.21 g (39%) of 4a.

Preparation of 3-(2-Hydroxy)ethyl-2,6-dimethylbenzothiazolium Bromide (4b). A solution of 2,6-dimethylbenzothiazole (13.0 g) and 2-bromoethanol (100 g) was stirred and heated in an oil bath to 120° C. for 96 hours. After cooling the reaction mixture to room temperature, adding ethyl acetate (150 ml) and stirring for 1 hour, the resultant solid was filtered and collected. The solid was then dissolved in methanol (150 ml) and charcoal (2 g) was added. The charcoal was removed by passing through a pad of Celite. The solution was then concentrated to a small volume and triturated with acetone (200 ml). The solid was collected, washed with acetone (2×30 ml), ethyl acetate (2×30 ml) and dried in an oven under high vacuum at 50 C. overnight to obtain 13.95 g (61%) of 4b.

Preparation of 3-(2-Hydroxy)ethyl-6-methoxy-2-methylbenzothiazolium Bromide (4c). A solution of 6-methoxy-2-methylbenzothiazole (1.82 g) and 2-bromoethanol (8.8 g) was stirred and heated in an oil bath at 120° C. for 74 hours. After cooling the reaction mixture to room temperature, adding ethyl acetate (25 ml) and stirring for 1 hour, the solid was filtered and collected. The solid was then dissolved in methanol (50 ml) and charcoal (0.5 g) was added. The charcoal was removed by passing through a pad of Celite. The solution was then concentrated to a small volume and triturated with ethyl acetate (100 ml). The solid was collected, washed with ethyl acetate (2×30 ml) and dried in an oven under high vacuum at 50° C. overnight to obtain 0.9 g (30%) of 4c.

Preparation of 3-(2-Hydroxy)ethyl-2-(2-N-phenyl) ethenylbenzothiazolium Bromide (5a). To a solution of 3-(2-hydroxy)ethyl-2-methylbenzothiazolium bromide (4a, 1.19 g) in a mixed solvent of methanol/ethanol (3:1, 80 ml) was added an excess of ethyl N-phenylformimidate (3.0 g) and the solution was stirred at room temperature for 36 h. The solvent was removed under reduced pressure to give a dry solid. The solid was subjected to column chromatography (silica gel, methylene chloride/methanol) purification. The fractions containing the product were combined and concentrated to dryness under reduced pressure. The solid was dissolved in methanol (10 ml) and precipitated with ethyl ether (200 ml). After drying at 50° C. under high vacuum overnight, 1.04 g (63%) of 5a was obtained as a yellow solid.

Preparation of 3-(2-Hydroxy)ethyl-6-methyl-2-(2-N-phenyl)ethenylbenzothiazolium Bromide (5b). To a solution of 3-(2-hydroxy)ethyl-2,6-dimethylbenzo-thiazolium bromide (4b, 2.76 g) in methanol (80 ml) was added an excess of ethyl N-phenylformimidate (3.6 g) and the solution stirred at room temperature for 36 hours. Ethyl acetate (160 ml) was then added and stirred overnight. The solid was collected, washed with ethyl acetate (2×30 ml) and dried. Drying the solid further in an oven at 50° C. under high vacuum overnight afforded 2.32 g (62%) of 5b as a yellow solid.

Preparation of 3-(2-Hydroxy)ethyl-6-methoxy-2-(2-N-phenyl)ethenylbenzothiazolium Bromide (5c). To a solution of 3-(2-hydroxy)ethyl-6-methoxy-2-methylbenzothiazolium bromide (4c, 0.79 g) in methanol (30 ml) was added an excess of ethyl N-phenylformimidate (1.5 g) and the solution was stirred at room temperature for 16 h. The solvent was removed under reduced pressure to yield a dry solid. The solid was subjected to column chromatography (silica gel), and eluted with a methanol/methylene chloride gradient (from 0 to 15% methanol). The fractions containing the product were combined and concentrated to dryness under reduced pressure. The solid was dissolved in methanol (5 ml) and precipitated with ethyl ether (150 ml). After drying in an oven at 50° C. under high vacuum overnight, 0.35 g (33%) of 5c as a yellow solid was obtained.

Preparation of Dye Compound 6 (Retic Red1). To a solution of 3-(2-hydroxy)ethyl-2-(2-N-phenyl) ethenylbenzothiazolium bromide (5a, 85.8 mg) and 1-(2-hydroxy)ethyllepidinium bromide (2, 58.4 mg) in methylene chloride (20 ml) was added triethylamine (91 µL) and acetic anhydride (62 µL). After stirring at room temperature for 2 hours the solvent was removed under reduced pressure to give a blue solid. The solid was partially redissolved in methanol (15 ml) and ethyl acetate (300 ml) was added. The resultant solid was collected via filtration, washed with ethyl acetate (2×30 ml) and dried. Further drying the solid in an oven at 50° C. under high vacuum overnight afforded 67.8 mg (66%) of 8 as a blue solid. Absorption spectrum maximum: 630 nm (in methanol), 640 nm (in DMSO).

Preparation of Dye Compound 7 (ReticRed6). To a solution of 3-(2-hydroxy)ethyl-6-methyl-2-(2-N-phenyl) ethenylbenzothiazolium bromide (5b, 85.6 mg), 1-(2-hydroxy)ethyllepidinium bromide (2, 58.7 mg) in methylene chloride (10 ml), and methanol (1.0 ml) was added triethylamine (91 µL) and acetic anhydride (61 µL). After stirring at room temperature for 2 hours the solvent was removed under reduced pressure to give a blue solid. The solid was partially redissolved in methanol (10 ml) and ethyl acetate (200 ml) was added. The resultant solid was collected via filtration, washed with ethyl acetate (2×30 ml) and dried. Further drying the solid in an oven at 50° C. under high vacuum overnight afforded 63.7 mg (60%) of 11 as a blue solid. Absorption spectrum maximum: 636 nm (in methanol), 645 nm (in DMSO).

C. Dye Stock Solution

To prepare a dye solution for analysis, stock solutions of dyes were prepared by separately dissolving a definite quantity of each dye compound in about 5 ml dimethylsulfoxide (DMSO) to provide a stock solution having a dye concentration of 5 mM.

D. Dye Spectroscopy

For spectroscopic measurements, sample solutions of the unbound dyes in PBS were prepared by diluting portions of the 5 mM stock solution of the dye in DMSO, prepared as described above, using phosphate-buffered saline (PBS). Specifically, in one experiment, the dye solutions were prepared by mixing approximately 2 µL of the 5 mM stock dye solution with 5 ml of PBS to give a final 2 μM dye concentration. 1 ml of the 2 μM dye solution was placed in a glass cuvette (Model 888-0105, Sienco, Wheat Ridge, Colo.). Fluorescence spectra of the samples were measured with a spectrofluorometer using an excitation wavelength of 648 nm.

Solutions of the dyes of this invention bound to RNA were prepared by combining 2 μl of the 5 mM stock solution of the dye and a 5 ml solution of RNA dissolved in PBS at a predetermined RNA concentration. 1 ml of each of the dye/RNA solutions was placed in a glass cuvette and fluorescence spectra of the samples measured using the spectrofluorometer and excitation wavelengths as described above.

E. Flow Cytometry for Red Excitable Dyes

An XL™ flow cytometer [Beckman Coulter Inc., Miami, Fla.] was used to conduct experiments described herein using the red-excitable dyes of the invention. The flow cytometer was modified from a standard XL™ flow cytometer by incorporating a HeNe laser (632.8 nm) and two red-sensitive photomultiplier tubes (PMT). Approximately 11.5 mW of 632.8 nm laser light from the above laser was incident on the beam shaping optics of the flow cytometer. Forward light scatter (FS), side scatter (SS) and one fluorescence (FL) parameter in the orthogonal direction were measured to analyze the red cells. The red cells were gated on a SS vs. FS dotplot. A fixed gate was then used to enumerate retics on a FL vs. FS dotplot.

F. Reference Analyses

Separate analyses for reticulocytes were performed using either (1) the standard Beckman Coulter reticulocyte reagents ReticONE™, which is based on a blue-excitable metachromatic fluorescent dye compound, employing a standard XL™ flow cytometer [Beckman Coulter Inc., Miami, Fla.] having a 488 nm argon laser as the illumination source, or (2) the conventional Retic-Count™ reticulocyte enumeration method (Becton Dickinson Cat. #349204) using Thiazole orange excited at 488 nm in a FACSCAN™ flow cytometer. For the ReticONE™ method, FS, SS, and two FL parameters were measured to analyze the red cells stained with the blue-excitable fluorescent dye contained in the ReticONE™ reagent. In this method, of the two FL parameters measured, one is measured at 525 nm, which corresponds to fluorescence due to the dye bound to DNA, and the other is measured at 675 nm, which corresponds to the dye bound to RNA. An automated gating algorithm, available in commercial XL™ flow cytometers, calculated reticulocyte percentage from a DNA vs. RNA fluorescence dotplot. This method is described in U.S. Pat. No. 5639,666.

For the Retic-Count™ method, FS, SS, and one FL parameter were measured to analyze the red cells stained with the blue-excitable fluorescent dye Thiazole Orange contained in the ReticCount™ reagent.

Example 2

Fluorescence Comparison of the Dyes of Present Invention in Bound and Unbound States In order to identify a fluorescent dye as a suitable candidate for reticulocyte enumeration, the fluorescence properties of several different compounds were determined. For reticulocyte enumeration, it is most desirable to have dyes that are weakly fluorescent when they are not bound to RNA, but show significant enhancement in fluorescence intensity when they are bound to RNA. However, it is not possible to predict which dye compound will have this ideal combination effects on its fluorescence activity both in absence and in presence of RNA. Significantly, the inventors found that the dyes of the present invention had favorable fluorescence properties required for sensitive detection of RNA.

For fluorescence measurements, a stock solution of each compound in DMSO was made (as described in Example 1C). A portion of this stock solution was diluted in PBS to obtain a dye concentration of 2 μM. 1 ml of this dilute solution was placed in a glass cuvette and the fluorescence spectra obtained exciting the dye at its excitation wavelength maximum. Next, 1 ml of a solution of free calf liver RNA (Sigma) dissolved in PBS at a concentration of 8 mg/ml, and a measured volume of the dye stock solution was mixed to obtain a dye concentration of 2 μM in the RNA solution. This dye solution diluted in the RNA solution was placed in a glass cuvette and the fluorescence spectra measured using the same excitation as in the previous measurement. As an example, FIG. 1A shows the comparison of the fluorescence spectra of the dye compound ReticRed1 in PBS solution with (see the upper curve) and without RNA (see the lower curve) present in the solution.

Figure 1B:
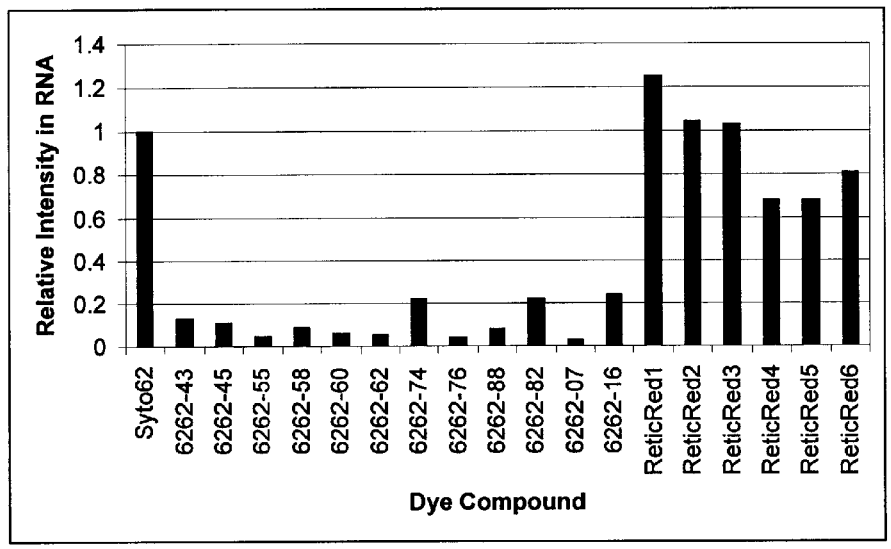
FIG. 1B is the comparison of the fluorescence intensity of the dyes of this invention and several other dyes studied during this experiment, relative to the fluorescence intensity of a commercial nucleic acid dye Syto 62 (Molecular Probes, Inc), all in presence of same amount of RNA in the solution.

In FIG. 1B, comparison of fluorescence intensity of several compounds in presence of RNA in solution are presented. In this FIG. 1B, the fluorescence intensities of the dyes are shown relative to the fluorescence intensity of a commercial dye Syto 62 (Molecular Probes Inc.) used herein as a reference standard. The structures of the additional compounds included in this study and shown in FIG. 1B but not already described above are shown in Table 2.

Figure 1C:
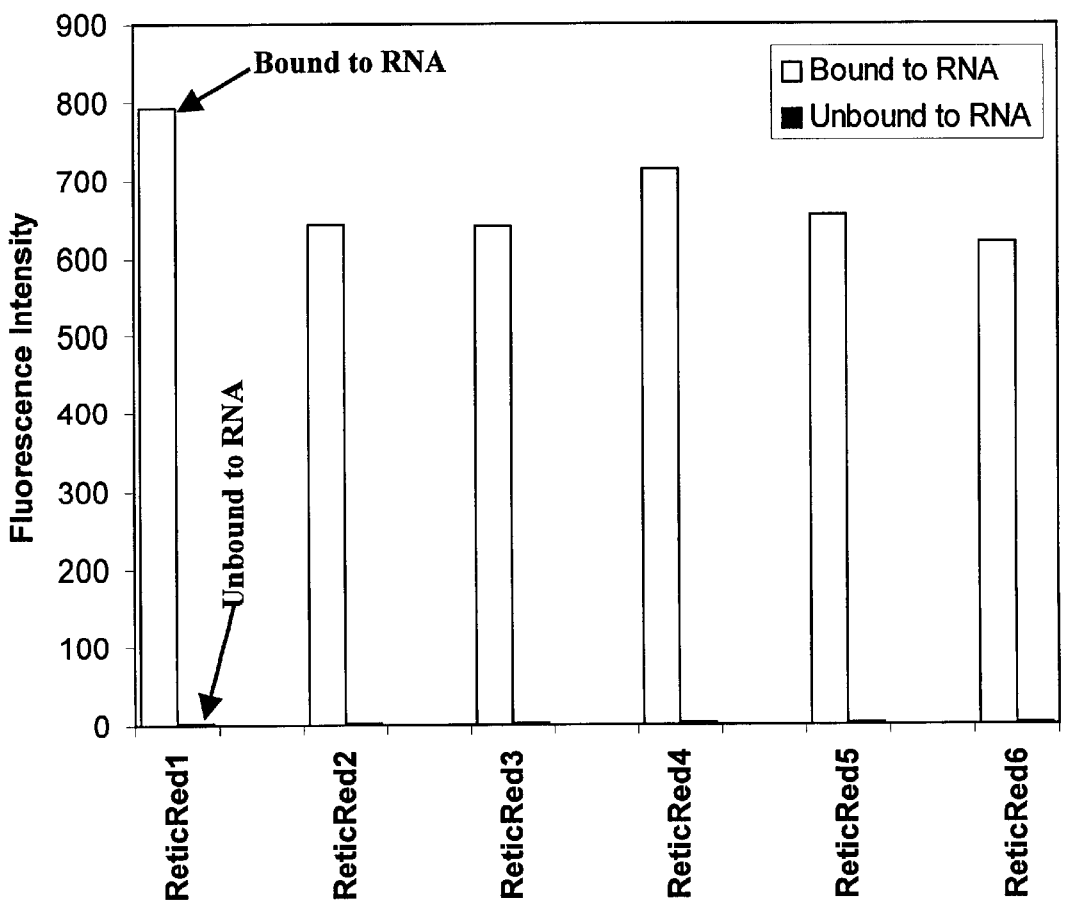
FIG. 1C shows the fluorescence intensities of the dyes, ReticRed1 through ReticRed6, of this invention in presence of 8 mg/ml RNA compared to their respective fluorescence intensities when there is no RNA present in the solution.

Table 1 compares the fluorescence intensities of the dyes of the present invention, ReticRed1 through ReticRed6 (concentration 2 μM), when they are not bound to RNA (unbound to RNA) and when they are in presence of RNA (bound to RNA). These intensities were obtained at the peak emission wavelengths of each fluorescence spectra measured as described above. FIG. 1C compares the fluorescence intensities of the RNA-bound and unbound dyes in graphical form.

TABLE 1

| DYE | Fluorescence Intensity | | Fluorescence enhancement ratio (Bound/Unbound) |
|---|---|---|---|
| | Unbound to RNA | Bound to RNA | |
| ReticRed1 | 2.49 | 791.23 | 317.763 |
| ReticRed2 | 1.72 | 643.77 | 374.285 |
| ReticRed3 | 1.28 | 639.68 | 499.75 |
| ReticRed4 | 1.72 | 713.4 | 414.767 |
| ReticRed5 | 2.24 | 656.06 | 292.884 |
| ReticRed6 | 2.75 | 619.2 | 225.164 |

TABLE 2

GS6262-43

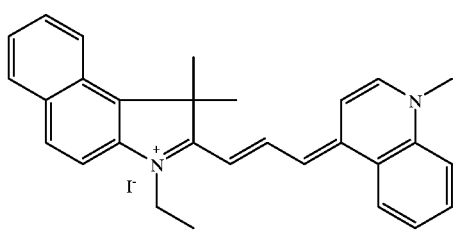

TABLE 2-continued
GS6262-45
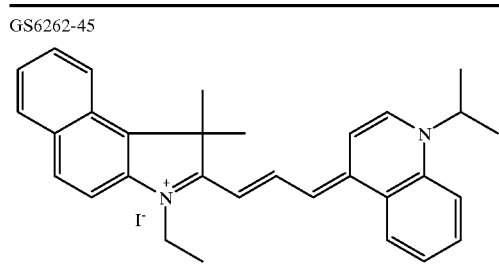
GS6262-55
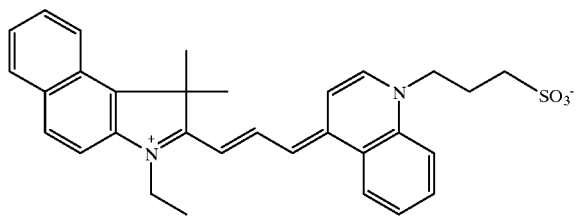
GS6262-58
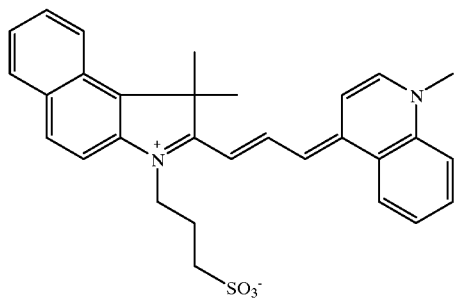
GS6262-60
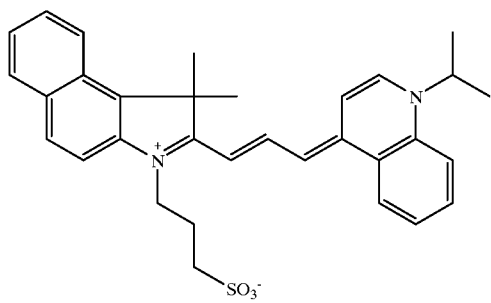
GS6262-62
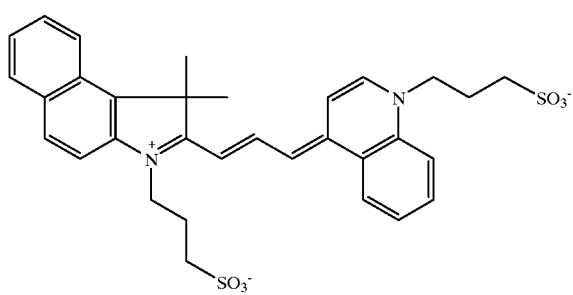
TABLE 2-continued
GS6262-82
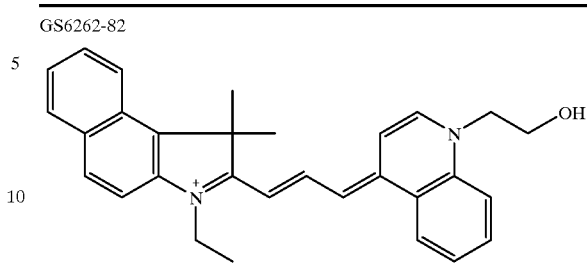
GS6262-88
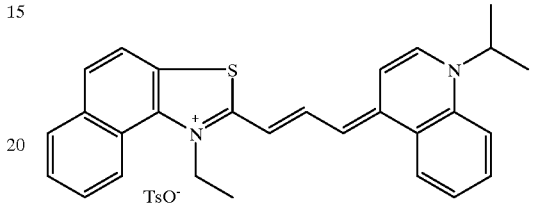
GS6262-07
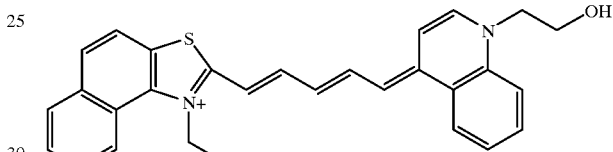
GS6262-76
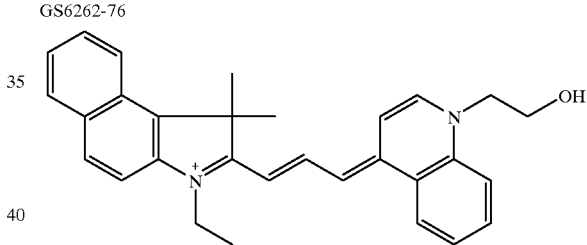
GS6262-74
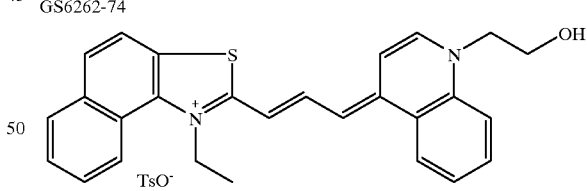
GS6262-16
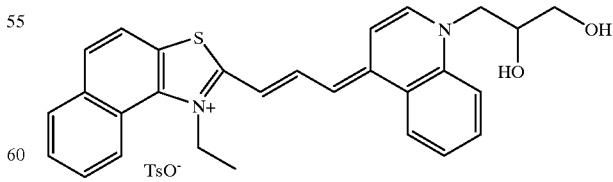
Example 3
Staining of Reticulocytes with ReticRed1 in Isotonic Saline Solution ISOFLOW™
A blood sample procured from a local hospital was used to determine the staining kinetics of ReticRed1 (prepared as described in Examples 1A and C) alone. The blood sample was first analyzed by two independent reference automated methods: the ReticONE™ method [described in Example 1E] and the New Methylene Blue method, a commercial method that is available for use in Gen*S™ instruments (Beckman Coulter). The ReticONE™ reference method gave a retic percentage of 7% and the Gen*S™ method gave a retic percentage of 6.7%.

For measurements using ReticRed1, 1 μl of whole blood was added to 1 ml of an isotonic saline solution containing a 5 μM ReticRed1 (diluted from the 5 mM stock solution described in Example 1C) solution and incubated for 10 and 40 minutes. The sample was then analyzed in a XL™ flow cytometer modified to incorporate a red HeNe laser (632.8 nm) as described in Example 1E.

Figure 2A:
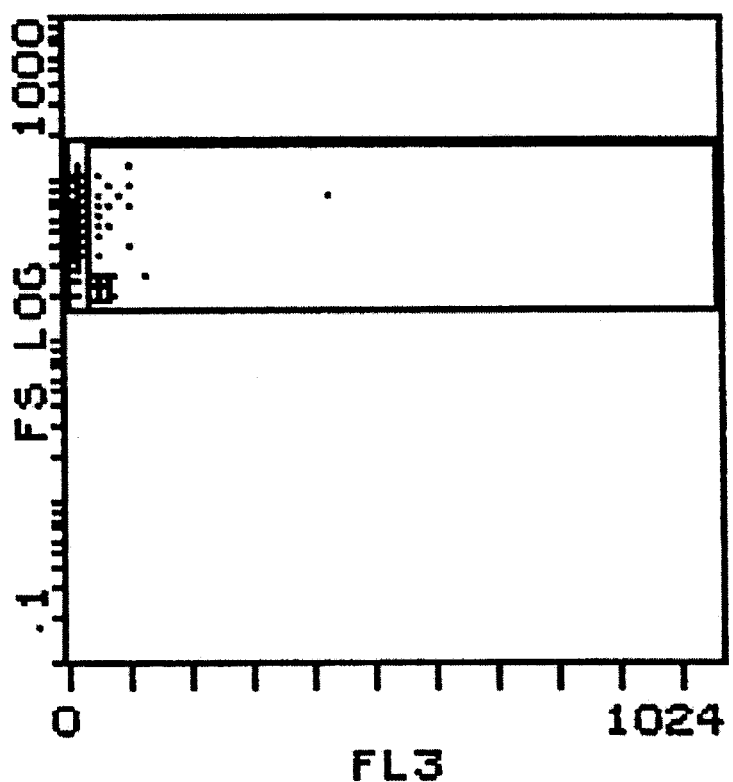
FIGS. 2A and 2B show the fluorescence from reticulocytes for an abnormal blood sample which were treated with the dye ReticRed1 in an isotonic saline solution without the presence of the rapid staining composition, and incubated for two different durations.
Figure 2B:
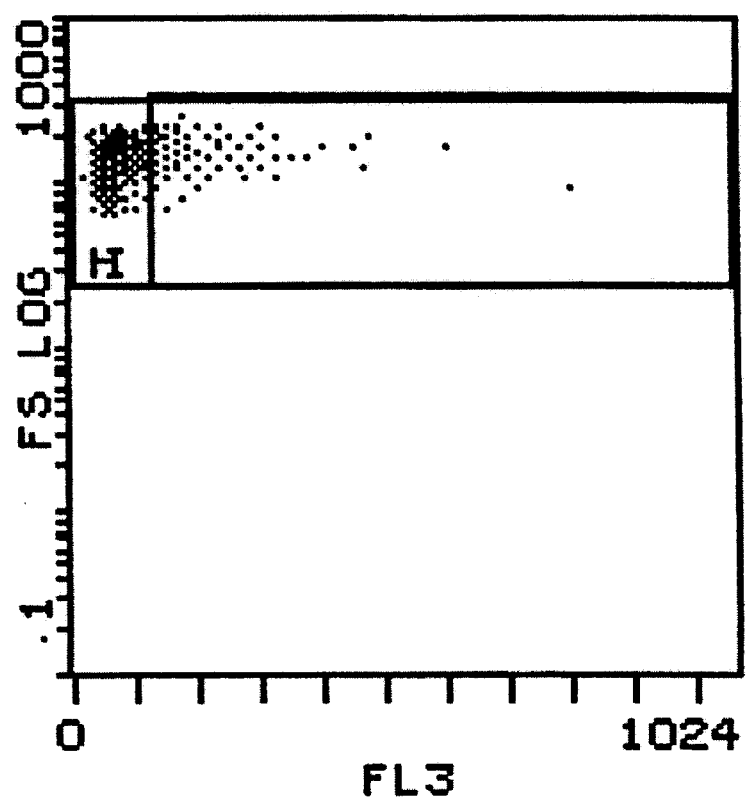

When whole blood was treated with ReticRed1 and analyzed in flow, red fluorescence in the 660 nm band resulted from a population of red cells, and indicated the presence of nucleic acid bound to ReticRed1 in such cells. This fluorescence is due to reticulocytes stained with ReticRed1. The flow cytometry data can be summarized according to incubation durations as follows: (a) 10 minutes: Total count 42660, Red Cells 32841, Reticulocytes 801, calculated retic percentage 2.4% (b) 40 minutes: Total count: 46199, Red cells 39713, Reticulocytes 2310, calculated retic percentage 5.8%. See, FIGS. 2A and 2B.

These results clearly demonstrate that the ReticRed1 dye alone requires a relatively long period of time to effectively stain the intracellular RNA.

Example 4

Rapid Staining of Reticulocytes with ReticRed1 using Whole Blood Samples

Although Example 3 above demonstrated that the dye ReticRed1 in an isotonic saline solution takes a relatively long time to stain reticulocytes, we found that using this dye to stain reticulocytes in presence of additional reagent compositions of this invention can reduce the incubation time for the staining significantly. Runs using four separate blood samples are presented to demonstrate rapid staining of reticulocytes by the dye ReticRed1.

A. Run1

1 μl of whole blood (from the same donor whose blood was used to conduct the analyses described in example 3 above) was added to 1 ml of a solution comprising a sphering reagent that spheres the red cells, the detergent Igepal (Sigma CA-630) at a concentration of 0.01%, the dye ReticRed1 at a concentration of 5 μM, and a solution of p-toluenesulfonic acid monohydrate at a final concentration of 5 μM, and incubated for about 1 minute. The sample was then analyzed in a XL flow cytometer modified to incorporate a red HeNe laser (632.8 nm). The sphering reagent is a solution comprising about 20 μg/ml Dodecyl-β-D-maltoside and 0.05% Proclin 300 in PBS at about pH 7.4 and about 290 mOsm.

Figure 3:
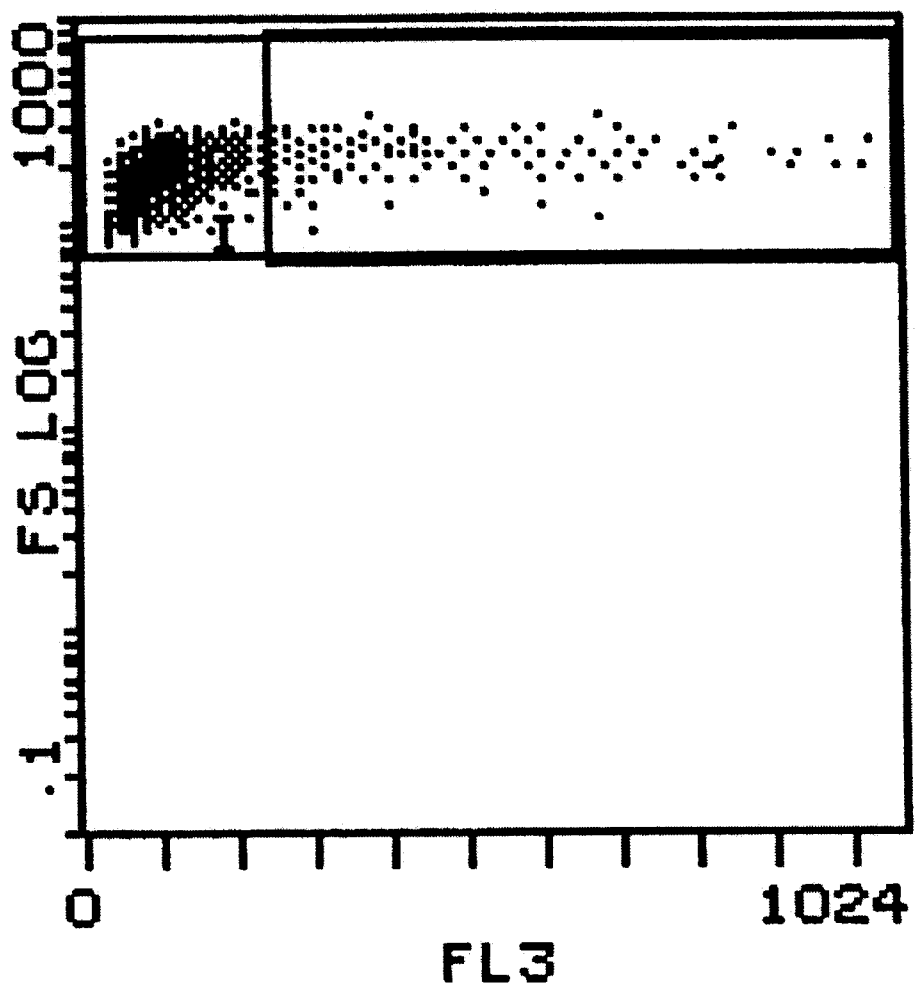
FIG. 3 shows the fluorescence from reticulocytes in the blood sample, from the same donor that was used in the experiments described in FIGS. 2A and 2B, after being treated with a composition of the invention containing the dye ReticRed1 and incubated for about 1 min. The percentage of reticulocytes enumerated by this method was 7.3%.

The sample so stained with ReticRed1 was then analyzed in a flow cytometer using 632.8 nm excitation from a HeNe laser. Bright red fluorescence in the 660 nm band resulted from the reticulocytes. The results of this experiment are shown in FIG. 3. The distribution of the cells in this dotplot, showing forward scatter versus fluorescence, is consistent with the distribution of mature red cells and reticulocytes previously shown by Tanke et. al. [cited above], in relation to their work on fluorescence based reticulocyte measurements. The percentage of reticulocytes enumerated by the present method was 7.3%.

B. Run 2

1 μl of whole blood from another abnormal donor was added to 1 ml of a solution comprising a sphering reagent (described in Example 4A, Run 1 above) that spheres the red cells, the detergent Igepal (Sigma CA-630) at a concentration of 0.01%, the dye ReticRed1 at a concentration of 5 μM, and a solution of p-toluenesulfonic acid monohydrate at a final concentration of 5 μM, and incubated for about 1 minute. The sample was then analyzed in a XL flow cytometer modified to incorporate a red HeNe laser (632.8 nm).

Figure 4:
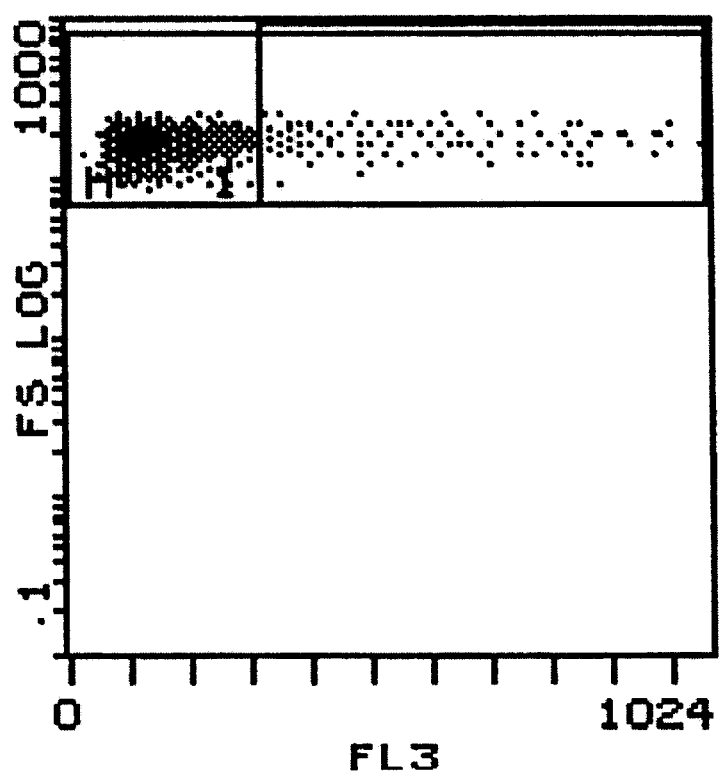
FIG. 4 shows the fluorescence from reticulocytes in an abnormal blood sample, after being treated with a composition of the invention containing the dye ReticRed1 and incubated for about 1 min. The percentage of reticulocytes enumerated by this method was 7.5%. The reference value for reticulocytes percentage obtained for this donor using an independent measurement method was 8%. The reagent composition in this example included Igepal, Dodecyl-β-D-maltoside and p-toluenesulfonic acid monohydrate.

The sample so stained with the dye ReticRed1 was then analyzed in a flow cytometer using 632.8 nm excitation from a HeNe laser. The result of this experiment is shown in FIG. 4. The distribution of the cells in this forward scatter versus fluorescence dotplot clearly shows the reticulocytes with high fluorescence intensity. The percentage of reticulocytes enumerated by this experiment was 7.5%. An independent reference value for reticulocyte percentage in this sample was 8%.

C. Run 3

Figure 5:
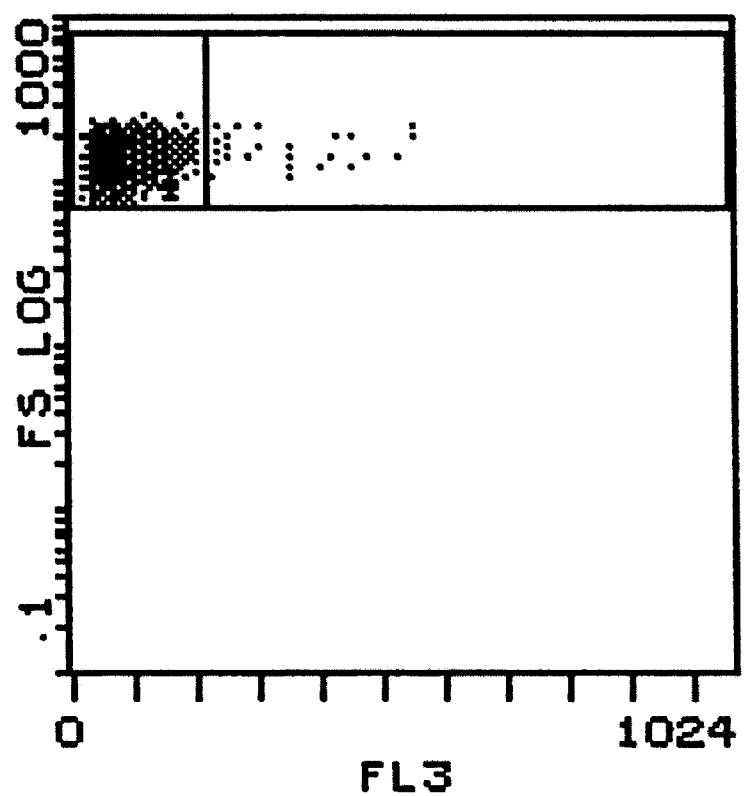
FIG. 5 shows the fluorescence from reticulocytes in the blood sample from a normal donor, after being treated with a composition of the invention containing the dye ReticRed1 and incubated for about 1 min. The percentage of reticulocytes enumerated by this method was 0.82%. The reagent composition in this example included Igepal, Dodecyl-β-D-maltoside and p-toluenesulfonic acid monohydrate. The reference value for reticulocyte percentage obtained for this donor using an independent measurement was 0.95%.

1 μl of whole blood from a normal donor was added to 1 ml of a solution comprising a sphering reagent (described in Example 4A, Run 1 above) that spheres red cells, detergent Igepal (Sigma CA-630) at a concentration of 0.01%, the dye ReticRed1 at a concentration of 5 μM, and a solution of p-toluenesulfonic acid monohydrate at a final concentration of 5 μM, and incubated for about one minute. The sample was then analyzed in a XL flow cytometer modified to incorporate a red HeNe laser (632.8 nm). The blood sample so stained with the dye ReticRed1 was analyzed in flow using 632.8 nm excitation from a HeNe laser. The result of this experiment is shown in FIG. 5. The reticulocyte percentage enumerated by this experiment was 0.82%. An independent reference measurement of the blood from the same donor using new methylene blue in a commercially available clinical hematology analyzer gave retic percentage of 0.95%.

D. Run 4

1 μl of abnormal whole blood from a donor was added to 1 ml of a solution comprising a sphering reagent (described in Example 4A, Run 1 above) that spheres red cells, detergent Igepal (Sigma CA-630) at a concentration of 0.01%, the dye ReticRed1 at a concentration of 5 μM, and a solution of sodium p-toluenesulfonate at a final concentration of 5 μM, and incubated for about one minute. The sample was then analyzed in a XL flow cytometer modified to incorporate a red HeNe laser (632.8 nm).

Figure 6:
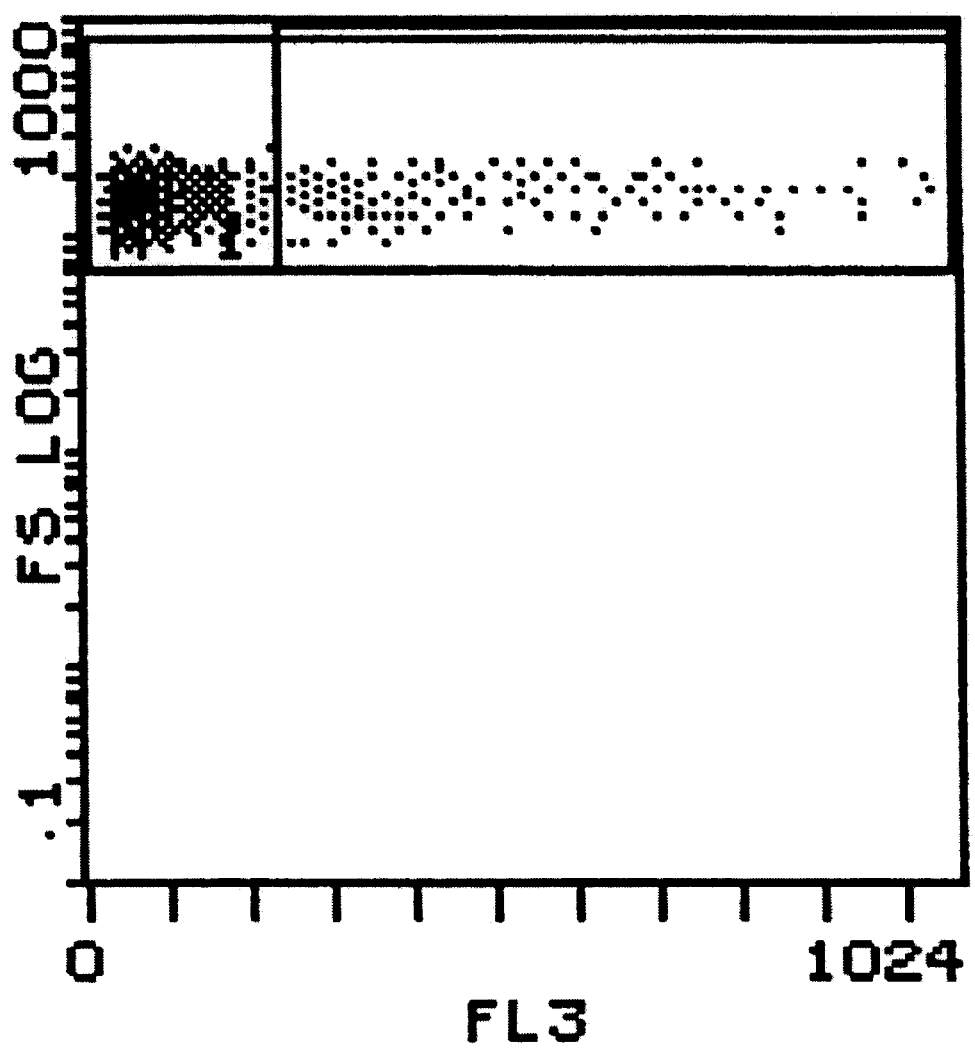
FIG. 6 shows the fluorescence from reticulocytes in an abnormal blood sample, after being treated with a composition of the invention containing the dye ReticRed1 and incubated for about 1 min. The percentage of reticulocytes enumerated by this method was 13.7%. The reference value for reticulocyte percentage obtained for this donor using an independent measurement was 13%. The reagent composition in this embodiment included Igepal, Dodecyl-β-D-maltoside and sodium p-toluenesulfonate.

The sample blood so stained with ReticRed1 was then analyzed in flow cytometer using 632.8 nm excitation from a HeNe laser. The result of this experiment is shown in FIG. 6. The reticulocyte percentage enumerated by this experiment was 13.7%. An independent reference method for this same sample gave a retic percentage value of 13%.

Example 5

Rapid Staining of Reticulocytes with ReticRed3 using Whole Blood Samples

A. Run 1

2 μl of whole blood from an abnormal donor having a high reticulocyte count was added to 1 ml of a solution comprising a sphering reagent (described in Example 4A, Run 1 above) that spheres the red cells, the detergent Igepal (Sigma CA-630) at a concentration of 0.01%, the dye ReticRed1 at a concentration of 5 μM, and a solution of sodium p-toluenesulfonate at a final concentration of 50 μM, and was gently mixed/incubated for about a second. The mixture was then aspirated into the XL flow cytometer containing the red HeNe laser for analysis.

Figure 7:
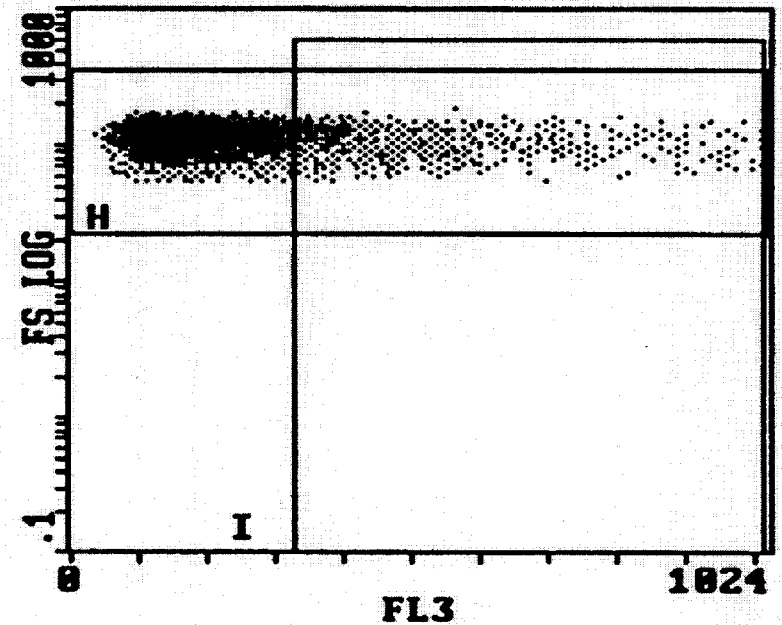
FIG. 7 shows the fluorescence from reticulocytes in an abnormal blood sample, after being treated with a composition of the invention containing the dye ReticRed3 and mixed for about 1 sec with no further incubation. The percentage of reticulocytes enumerated by this method was 13.8%. An independent reference value for reticulocyte percentage obtained for this sample by a conventional ReticCount™ method was approximately 13.3%. The reagent composition in this embodiment included Igepal, Dodecyl-β-D-maltoside and sodium p-toluenesulfonate.

The result of this experiment is shown in FIG. 7, where the reticulocytes are distinguished from the mature red blood cells by the higher fluorescence intensities associated with them. The percentage of reticulocytes enumerated by this experiment was 13.8%. An independent reference value for reticulocyte percentage measured for this sample using the conventional ReticCount™ reticulocyte enumeration method (using Thiazole orange excited at 488 nm) in a FACSCAN flow cytometer was 13.3%.

B. Run 2

2 μl of whole blood from an abnormal donor having low reticulocyte counts was added to 1 ml of a solution comprising a sphering reagent (described in Example 4A, Run 1 above) that spheres the red cells, the detergent Igepal (Sigma CA-630) at a concentration of 0.01%, the dye ReticRed1 at a concentration of 5 μM, and a solution of sodium p-toluenesulfonate at a final concentration of 50 μM, and was gently mixed/incubated for about a second. The mixture was then aspirated into the XL flow cytometer containing the red HeNe laser for analysis.

Figure 8:
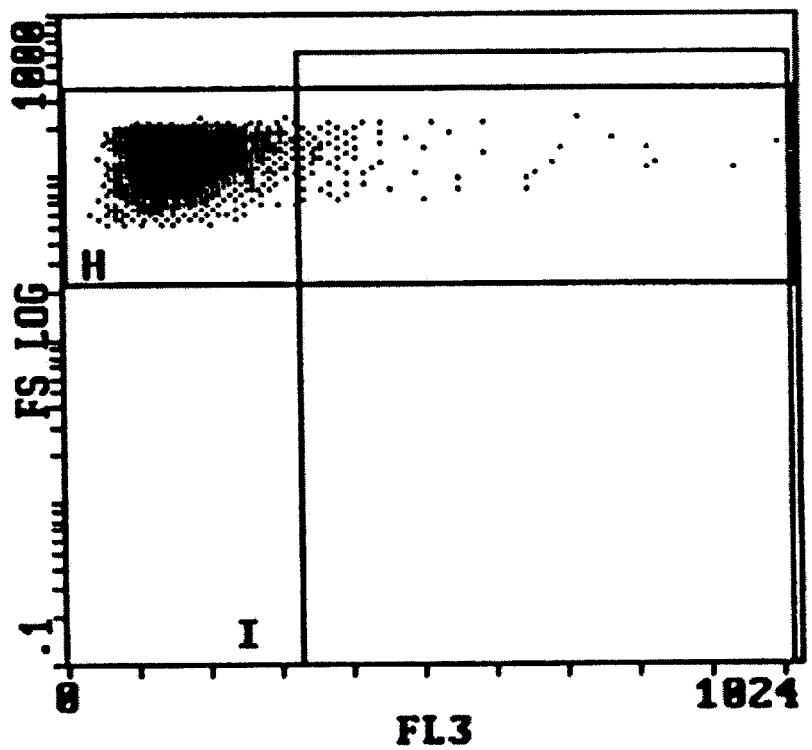
FIG. 8 shows the fluorescence from reticulocytes for in abnormal blood sample, after being treated with a composition of the invention containing the dye ReticRed3 and mixed for about 1 sec with no further incubation. The percentage of reticulocytes enumerated by this method was 1%. An independent reference value for reticulocyte percentage obtained for this sample by a conventional ReticCount™ method was approximately 1.3%. The reagent composition in this embodiment included Igepal, Dodecyl-β-D-maltoside and sodium p-toluenesulfonate.

The result of this experiment is shown in FIG. 8. The percentage of reticulocytes enumerated by this experiment was 1%. An independent reference value for reticulocyte percentage measured for this sample using the conventional ReticCount™ reticulocyte enumeration method (Thiazole orange excited at 488 nm) in a FACSCAN flow cytometer was 1.3%.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A dye composition comprising
   (a) a dye having the formula:

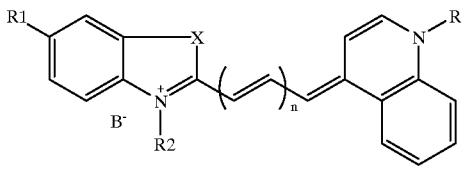

wherein,
   n is 0, 1, 2, or 3; R1 is H, alkyl, or an alkoxy group; R2 is $CH_2(CH_2)_mOH$, wherein m is 0, 1, 2, or 3; X is O, S, or $C(CH_3)_2$; R is $CH_3$, $CH(CH_3)_2$, $CH_2CH_2OH$, alkyl, alkylsulfonate, or hydroxyalkyl and B− is a counteranion; and
   (b) one or more components selected from the group consisting of a surfactant, a preservative and a sulfonic acid or a salt thereof.

2. The dye composition according to claim 1, wherein n is 1, $R_1$ is H, R is $CH_2CH_2OH$, R2 is $CH_2CH_2OH$, and X is S.

3. The dye composition according to claim 1, wherein n is 1, $R_1$ is H, R is $CH(CH_3)_2$, $R_2$ is $CH_2CH_2OH$ and X is S.

4. The dye composition according to claim 1, wherein n is 1, $R_1$ is H, R is $CH_3$, $R_2$ is $CH_2CH_2OH$, and X is S.

5. The dye composition according to claim 1, wherein n is 1, $R_1$ is $CH_3$, R is $CH_3$, $R_2$ is $CH_2CH_2OH$, and X is S.

6. The dye composition according to claim 1, wherein n is 1, $R_1$ is $CH_3$, R is $CH(CH_3)_2$, $R_2$ is $CH_2CH_2OH$, and X is S.

7. The dye composition according to claim 1, wherein n is 1, $R_1$ is $CH_3$, R is $CH_2CH_2OH$, $R_2$ is $CH_2CH_2OH$, and X is S.

8. The dye composition according to claim 1, wherein said component is a surfactant.

9. The dye composition of claim 8, wherein said surfactant comprises a non-ionic surfactant.

10. The dye composition of claim 9, wherein said non-ionic surfactant is selected from the group consisting of dodecyl-β-D-maltoside, N,N-bis[3-D-glucon-amidopropyl] cholamide, polyoxypropylene-polyoxyethylene block copolymer, N-Tetradecyl-β-D-maltoside, Daconyl-N-methyl-glucamide, n-Dodecyl-β-D-glucopyranoside, n-Decyl-β-D-glucopyranoside, polyethylene glycol ester of stearic acid, ethoxylated cocomonoglyceride, octyphenoxy-poly (ethyleneoxy) ethanol, ethoxylated octylphenol, and linear alcohol.

11. The dye composition of claim 8, wherein said surfactant comprises a cationic surfactant.

12. The dye composition of claim 11, wherein said cationic surfactant is selected from the group consisting of coco hydroxyethyl imidazoline, lauryltrimethylammonium chloride, decyltrimethylammonium bromide, and octyltrimethylammonium bromide.

13. The dye composition of claim 8, wherein said surfactant comprises an anionic surfactant.

14. The dye composition of claim 13, wherein said anionic surfactant is selected from the group consisting of ammonium perfluoralkyl carboxylate, and sodium lauroyl myristoyl lactylate.

15. The dye composition of claim 8, wherein said surfactant comprises a zwitterionic surfactant.

16. The dye composition of claim 15, wherein said zwitterionic surfactant is selected from the group consisting of lauramidopropyl betaine, N-tetradecyl-N,N-dimethyl-3-ammonio-1-propanesulfonate, N-dodecyl-N,N-dimethyl-3-ammonio-1-propanesulfonate, cocoamidopropylbetaine, cocoamidosulfobetaine, N-dodecyl-N,N-dimethyl-3-ammonio-1-propanesulfonate, and N-tetradecyl-N,N-dimethyl-3-ammonio-1-propanesulfonate.

17. The dye composition according to claim 1, further comprising a detergent in an amount of about 0 up to about 1% by volume.

18. The dye composition according to claim 17, wherein said detergent is selected from the group consisting of octylphenoxypoly (ethyleneoxy) ethanol, ethoxylated octylphenol, and linear alcohol alkoxylates.

19. The dye composition according to claim 1, wherein said component is a sulfonic acid or a salt thereof.

20. The dye composition of claim 19, wherein said sulfonic acid is p-toluenesulfonic acid.

21. The dye composition according to claim 20, wherein concentration of said p-toluenesulfonic acid is about 0 to about 250 μM.

22. The dye composition according to claim 19, wherein said sulfonate salt is selected from the group consisting of sodium p-toluenesulfonate, silver p-toluenesulfonate, and zinc p-toluenesulfonate.

23. The dye composition according to claim 22, wherein concentration of said sodium p-toluenesulfonate is about 0 to about 250 μM.

24. The dye composition according to claim 1, wherein said component is a preservative.

25. The dye composition according to claim 24, wherein said preservative comprises 5-Chloro-2-methyl-4-isothiazolin-3-one and 2-methyl-4-isothiazolin-3-one.

26. A method for staining nucleic acids comprising contacting a sample of nucleic acids with the dye composition of claim 1.

27. A method for staining reticulocytes comprising contacting a sample of reticulocytes with the dye composition of claim 1.

28. A method for staining nucleic acid comprising the step of contacting a sample containing nucleic acid with a dye having the formula:

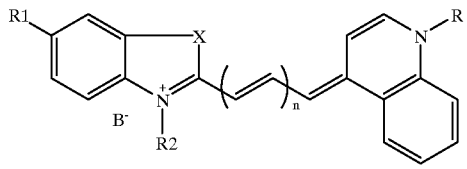

wherein, n is 0, 1, 2, or 3; R1 is H, alkyl, or an alkoxy group; R2 is $CH_2(CH_2)_mOH$, wherein m is 0, 1, 2, or 3; X is O, S, or $C(CH_3)_2$; R is $CH_3$, $CH(CH_3)_2$, $CH_2CH_2OH$, alkyl, alkylsulfonate, or hydroxyalkyl and B– is a counteranion.

29. The method according to claim 28, wherein said sample comprises cells, and wherein said sample is contacted by the dye in the presence of a surfactant.

30. The method according to claim 28, wherein said sample comprises whole blood.

31. A method for analysis of reticulocytes comprising the steps of:

(a) contacting a sample containing reticulocytes with a compound having the formula:

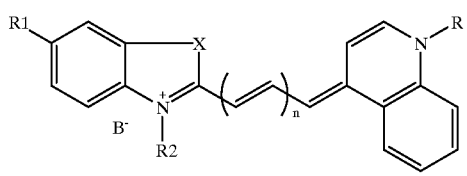

wherein, n is 0, 1, 2, or 3; R1 is H, alkyl, or an alkoxy group; R2 is $CH_2(CH_2)_mOH$, wherein m is 0, 1, 2, or 3; X is O, S, or $C(CH_3)_2$; R is $CH_3$, $CH(CH_3)_2$, $CH_2CH_2OH$, alkyl alkylsulfonate, or hydroxyalkyl and B– is a counteranion, such that the reticulocytes are stained by the said compound; and (b) analyzing the stained reticulocytes by flow cytometry to detect the presence of reticulocytes.

32. The method according to claim 31, wherein said analysis by flow cytometry includes measurement of one fluorescence parameter and at least one parameter selected from the group consisting of light scatter, optical absorption, axial light loss, DC electrical impedance, and radio frequency (RF) conductivity and combinations thereof.

33. A method for facilitating transport of a dye composition through a cell membrane comprising the steps of (a) admixing a sample comprising a cell with 1) a dye having the formula:

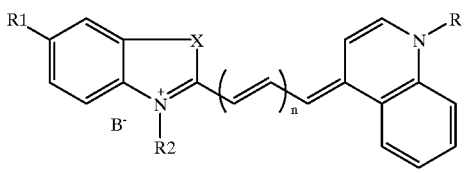

wherein, n is 0, 1, 2, or 3; R1 is H, alkyl, or an alkoxy group; R2 is $CH_2(CH_2)_mOH$, wherein m is 0, 1, 2, or 3; X is O, S, or $C(CH_3)_2$; R is $CH_3$, $CH(CH_3)_2$, $CH_2CH_2OH$, alkyl, alkylsulfonate, or hydroxyalkyl and B– is a counteranion, 2) a surfactant, and 3) a sulfonic acid or salt thereof, and (b) incubating the admixed sample of (a) for up to about one minute.

34. The method according to claim 33, wherein said incubation is conducted in the temperature range of about 20° C. to about 40° C.

* * * * *